United States Patent [19]

McAdams et al.

[11] Patent Number: 5,466,256
[45] Date of Patent: Nov. 14, 1995

[54] MULTI-FUNCTION MULTI-ELECTRODE DEVICE

[76] Inventors: Eric T. McAdams, Ormsdale, 52 Cable Road, Whitehead, County Antrim, Ireland, BT38 9PZ; John M. Anderson, 16 Torgrange, Hollywood, County Down, BT18 0NG, Ireland; James A. McLaughlin, 9 Hampton Gardens, Hampton Court Village, Belfast, BT7 2DF, Ireland

[21] Appl. No.: 150,980

[22] Filed: Nov. 12, 1993

[30] Foreign Application Priority Data

Nov. 13, 1992 [IE] Ireland ................................ 922818

[51] Int. Cl.⁶ .................................................. A61N 1/04
[52] U.S. Cl. ........................................... 607/142; 128/640
[58] Field of Search ................................ 128/639, 640; 607/142, 152, 149

[56] References Cited

U.S. PATENT DOCUMENTS 4,583,548   4/1986   Schmid ................................ 128/639

Primary Examiner—William E. Kamm
Assistant Examiner—Scott M. Getzow
Attorney, Agent, or Firm—Sughrue, Mion, Zinn, Macpeak & Seas

[57] ABSTRACT

A device usable as a cardiac pacing electrode and as a cardiac defibrillation electrode has first and second substantially parallel electrodes (1,4), a first gel pad (3) located between the first and second electrodes, and a second gel pad (5) located on the second electrode. The first electrode (1) and the first and second gel pads (3, 5) may function as a cardiac pacing electrode and the second electrode (4) and the second gel pad (5) may function as a cardiac defibrillation electrode.

17 Claims, 1 Drawing Sheet

MULTI-FUNCTION MULTI-ELECTRODE DEVICE

BACKGROUND OF THE INVENTION

This invention relates to a multi-function multi-electrode device. In particular, it relates to a multi-function multi-electrode device for medical use.

Defibrillation is used to depolarize cardiac muscle fibres by means of a large electric shock in an attempt to re-establish normal cardiac rhythm. A large current of up to 50 A and several thousand volts is typically applied to a patient, using a damped sinusoidal waveform with a duration of approximately 5–10 ms, or a truncated exponential waveform of 5–30 ms duration.

External cardiac pacing stimulates the heart at regular intervals to enable control of the heart rate when the intrinsic cardiac rate is not sufficient. External cardiac pacemakers apply modest levels of current (50–200 mA) and voltage to a patient, using rectangular or truncated exponential current pulses having durations of 10–40 ms.

Due to their differing operating conditions, electrodes for cardiac defibrillation and external pacing have differed in design. In external pacing, for example, a major problem is that a substantial portion of the applied current flows into the patient via the peripheral areas of the electrode rather than there being a uniform current density over the electrode surface. This is referred to as the perimeter effect and the large local current densities at the periphery can result in serious skin burns and cutaneous pain at the electrode edges. In order to ensure a more uniform current density distribution and thus avoid or minimise the above problems, relatively thick, wide, high-resistance gel pads have been used.

The use of high impedance gel pads, however, results in significantly lower delivered current, and thus may limit the effectiveness of cardiac defibrillation attempts. The passage of large currents through such high impedances gives rise to a significant temperature rise and can be accompanied by spark generation which, in the presence of oxygen, is extremely dangerous.

Fires during resuscitation attempts have been reported in the literature. Low resistance gel pads are therefore commonly used in external defibrillation electrodes.

Two different electrode systems are therefore generally used for cardiac defibrillation and external cardiac pacing. This is less than optimal as two sets of electrodes may be required for a patient. Such a cumbersome arrangement would also tend to be relatively expensive.

In U.S. Pat. No. 4,776,350 (Grossman) there is disclosed an electrode comprising two parallel electrically conductive in-contact members. In order to minimise the current density concentrations around the electrode edge, the first conductive member has an area resistivity much less than that of the second conductive member. The conductive members are composed of a conductive polymer such as a carbon filled vinyl or carbon filled rubber material. The resistivities of the two conductive members depend upon the application to which the electrode is to be put. Hence the electrode may be used as a cardiac pacing electrode or as a cardiac defibrillation electrode.

In a preferred arrangement of the invention described in U.S. Pat. No. 4,776,350, the second conductor member comprises a laminate composed of an electrically conductive rubber sheet, sandwiched between two layers of conductive gum adhesive. The area resistivity of the rubber layer is greater than the area resistivity of each gum adhesive layer. It is believed that current tends to flow preferentially through areas of the poorly mixed gum adhesive which have higher concentrations of conductive substances. It is thought that the incorporation of a layer of a high resistance rubber between layers of conductive gum adhesive will reduce the tendency of this form of current "hot spot" production. The current still has to flow through the bottom layer of gum adhesive with all of its "hot spots". The gum adhesive layers and the conductive layers appear to have the same areas.

The above arrangement gives rise to a very resistive electrode device, potentially suitable for cardiac pacing but less than optimal as a defibrillation electrode.

In *"Electrodes and the measurement of bioelectric events"*, Geores, L. A. Wiley—*Interscience*, New York, 1972, it is known to provide a "guard-ring" electrode which comprises a pair of coplanar electrodes which are electrically isolated from each other. Essentially, one electrode is located concentrically relative to the other electrode. The outer electrode is used to modify the current density distribution of the inner electrode. Both electrodes are operated at the same potential to enable the inner or smaller electrode to be used for current measurement. The outer electrode, known as the guard electrode aids in providing a uniform current-density distribution around the main current path in the specimen. The current flowing in the guard electrode is not measured. However, a disadvantage of such an arrangement is that the current density of the outer electrode is not uniform and, accordingly, this electrode arrangement is only of benefit if the inner electrode is used for measurement purposes.

It is an object of the present invention to overcome these problems.

SUMMARY OF THE INVENTION

The invention, therefore, provides a multi-function multi-electrode device which comprises first and second electrically conductive electrodes in substantially parallel spaced apart relationship, a first gel pad located between the first and second electrodes, a second gel pad located on or adjacent to the second electrode, the second gel pad being exposed or exposable for making contact with a patient, and means for making electrical connection to each of the electrodes, whereby the first electrode and the first and second gel pads may function as a cardiac pacing electrode and the second electrode and the second gel pad may function as a cardiac defibrillation electrode.

BRIEF DESCRIPTION OF THE DRAWINGS

The invention will be understood in greater detail from the following description of a preferred embodiment thereof given by way of example only and with reference to the accompanying drawings, in which.

DETAILED DESCRIPTION OF THE PREFERRED EMBODIMENT

Figure 2:
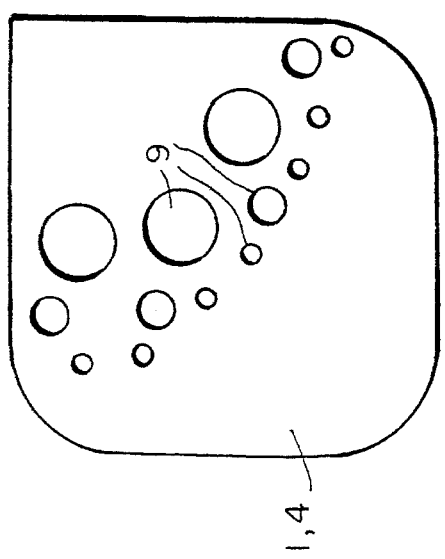
FIG. 2 is a top view of the first and/or second electrodes.
Figure 1:
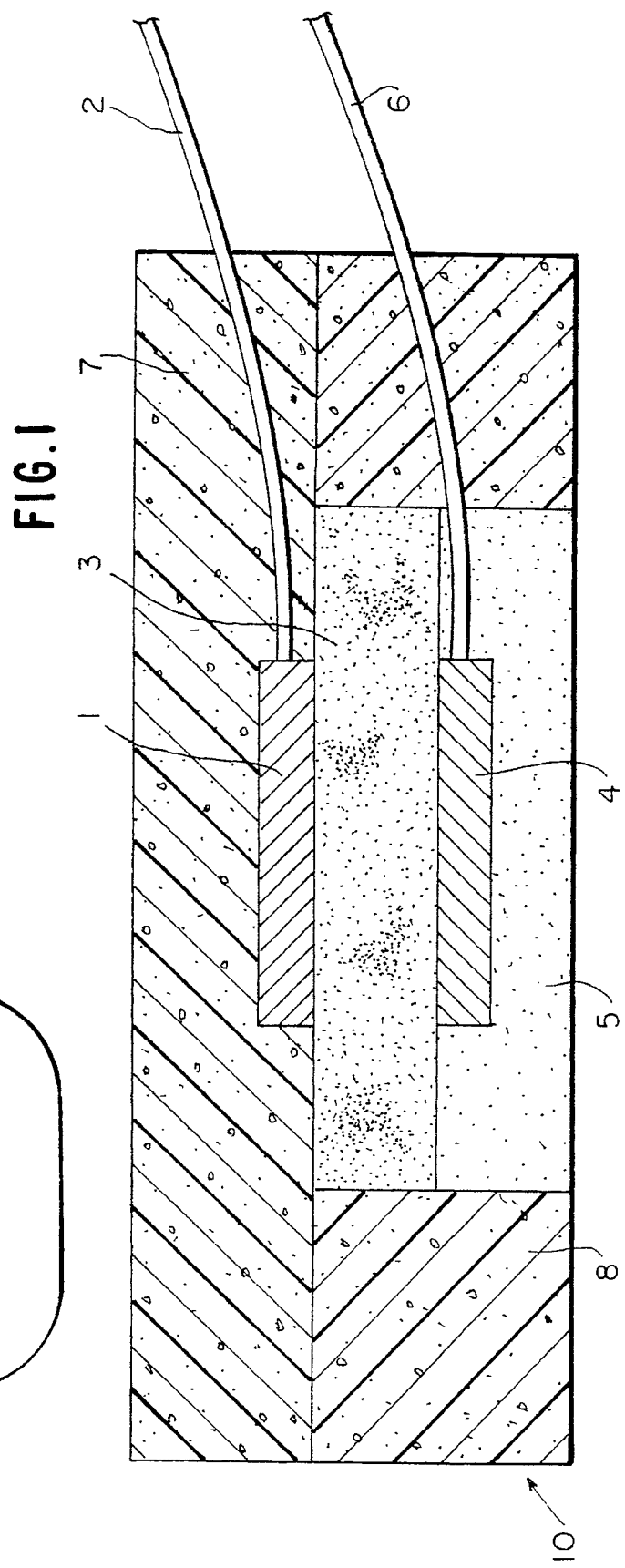
FIG. 1 is a cross-sectional view of an electrode according to the invention.

Referring now to the drawings there is shown a multi-function multi-electrode 10 according to the invention which comprises a first electrically conductive electrode or plate 1, and a second electrically conductive electrode or plate 4, the plates 1 and 4 having respective electrical connection leads 2 and 6. The plate 1 is located on a gel pad 3 of relatively high electrical resistivity, and the second plate 4 is located on the opposite surface of the gel pad 3. A relatively low electrical resistivity gel pad 5 covers the second conductive plate 4, embedding the plate 4 within the interior of the two gel pads 3 and 5. The first plate 1 and the second plate 4 are located in substantially parallel spaced apart relationship. Medical grade adhesive foam layers 7 and 8 cover and electrically insulate the first conductive plate 1 and also surround the edges of the gel pads 3 and 5. The layers 7, 8 also serve to adhere the total structure firmly to a patient. The underside of gel pad 5 makes physical and electrical contact with the patient. When not in use, the underside of gel pad 5 and of the surrounding foam layer 8 are protected by a release layer (not shown). The second plate 4 and the low impedance gel pad 5 serve as the defibrillation electrode. The outer edge of the second plate 4 may be so shaped with indentations and/or projections as to substantially increase the length of the peripheral edge of the plate 4 (compared to a square or circular electrode of the same area) and thus reduce the peripheral current density. The second plate 4 may include a plurality of apertures 9 or matrix of openings so as to promote a more uniform current density distribution, as shown in FIG. 2. This may, for example, be achieved by distributing the apertures in such a way as to promote a progressively higher electrical resistance of the plate 4, towards its periphery. Plate 1 may also be similarly formed to promote a more uniform current density distribution.

The first plate 1, the high impedance gel pad 3 and the low impedance gel pad 5 form the cardiac pacing electrode. The combination of the two gel pads 3, 5 gives rise effectively to a thick, high resistance pad, ideal for pacing purposes. Due to the extra thickness provided by the use of the two gel pads 3 and 5 in this case, the gel pad 3 need not necessarily have a higher resistivity compared with that of the gel pad 5.

During the pacing mode, the second plate 4 can serve to further distribute current densities throughout the gel pad 5 and thus minimise current density "hot spots". The openings in the second plate 4 may optimise the distribution of current densities and in one embodiment of the invention, the central portion of the second plate 4 may be totally removed giving rise to a hollow, annular-like design. The first plate 1 may also contain a plurality of apertures to help optimise the current density distribution.

The gel pad 5 may be larger in area than either the gel pad 3 or first plate 1 in order to help optimise current density distribution.

In order to avoid corrosion problems, the edges of the second plate 4 may be coated with an insulating layer (not shown). The insulating layer may totally or partially coat the side of the second plate 4 which makes contact with the gel pad 3 in order to further optimise the current density distribution.

Biosignals, such as the electrocardiogram, may be sensed using the first electrode or plate 1, the second electrode or plate 4, or both. When the need arises, the patient may be defibrillated using an impulse applied via the second plate 4 and the means of connection 6. When necessary, the patient may be paced externally by impulses applied via the first plate 1 and the means of connection 2. Changing from one mode of operation to another does not require the removal and replacement of an electrode set or two sets of electrodes but is simply achieved, for example, by means of a switch on the monitoring/defibrillation/pacing apparatus.

Plates 1 and 4 may both be used simultaneously to apply either a defibrillation or pacing impulse. The same electrical signal may be applied to both plates 1,4 or different signals may be applied to each of the plates 1,4. For example, during the pacing mode of operation, a modified version of the electrical signal (impulse) applied to the first plate 1 may be applied to the second plate 4 in order to optimise the current density distribution in the patient's skin, thus minimising trauma to the patient and maximising the efficiency of the pacing impulse. In the above example, the impulse applied to the second plate 4 may differ in amplitude, polarity and/or waveform to that applied to the first plate 1.

In the present invention, the current density distribution in the patient's skin, due to the contributions of both electrodes 1, 4 is of interest. It is for this reason that different impulses may be applied to each of the plates 1, 4. The impulse applied to the second plate 4 must be sufficient to modify the electrical field under the first plate 1 while avoiding large current densities under the second plate 4. The optimal relationship between the impulses applied to the two plates 1, 4 is greatly influenced by the relative dimensions, shapes and electrical properties of the conductive plates 1 and 4 and respective gel pads 3 and 5 as well as the electrical properties of the skin and the specific application.

The invention is not limited by or to the specific embodiment described which can undergo considerable variation without departing from the scope of the invention.

We claim:

1. A multi-function multi-electrode cardiac device for applying electrical signals to a living body, comprising: first and second substantially planar, electrically conductive electrodes disposed in a substantially parallel spaced apart relationship, a first gel pad disposed between facing sides of the first and second electrodes, a second gel pad disposed on an opposite side of the second electrode and having an exposed surface for making contact with a patient, each of the first and second gel pads having an area greater than that of the second electrode such that the first and second gel pads contact one another laterally of the second electrode, and means for individually making direct electrical connection to each of the electrodes, wherein the first electrode and the first and second gel pads comprise a cardiac pacing electrode assembly and the second electrode and the second gel pad comprise a cardiac defibrillation electrode assembly.

2. A device as claimed in claim 1, wherein the first gel pad has a higher resistivity than the second gel pad.

3. A device as claimed in claim 1, wherein edges of the second electrode are coated with an insulating layer.

4. A device as claimed in claim 3, wherein the insulating layer also at least partially coats the surface of the second electrode in contact with the first gel pad.

5. A device as claimed in claim 1, wherein the second electrode includes a plurality of apertures to promote a more uniform current density distribution therein.

6. A device as claimed in claim 5, wherein the apertures are distributed so as to provide a progressively higher electrical resistance of the second electrode towards the periphery thereof.

7. A device as claimed in claim 1, wherein the second electrode is annular.

8. A device as claimed in claim 1, wherein the first electrode includes a plurality of apertures to promote a more uniform current density distribution therein.

9. A device as claimed in claim 1, further including an adhesive foam layer covering the first electrode and edges of the first and second gel pads.

10. A device as claimed in claim 9, further including a protective layer releasably covering the second electrode and the portion of the foam layer surrounding it.

11. A device as claimed in claim 1, wherein the area of the second gel pad is greater than the area of the first gel pad.

12. A device as claimed in claim 1, further comprising means for enabling an electrical signal to be applied to the second electrode in order to modify the distribution of current density flowing from the first electrode.

13. A multi-function multi-electrode device which comprises first and second electrically conductive electrodes in substantially parallel spaced apart relationship, a first gel pad located between the first and second electrodes, a second gel pad located on or adjacent to the second electrode, the second gel pad being exposed or exposable for making contact with a patient, the first gel pad having a higher resistivity than the second gel pad, and means for making electrical connection to each of the electrodes, whereby the first electrode and the first and second gel pads may function as a cardiac pacing electrode and the second electrode and the second gel pad may function as a cardiac defibrillation electrode.

14. A multi-function multi-electrode device which comprises first and second electrically conductive electrodes in substantially parallel spaced apart relationship, a first gel pad located between the first and second electrodes, a second gel pad located on or adjacent to the second electrode, edges of the second electrode being coated with an insulating layer and the second gel pad being exposed or exposable for making contact with a patient, and means for making electrical connection to each of the electrodes, whereby the first electrode and the first and second gel pads may function as a cardiac pacing electrode and the second electrode and the second gel pad may function as a cardiac defibrillation electrode.

15. A multi-function multi-electrode device which comprises first and second electrically conductive electrodes in substantially parallel spaced apart relationship, a first gel pad located between the first and second electrodes, a second gel pad located on or adjacent to the second electrode, the second gel pad being exposed or exposable for making contact with a patient, and means for making electrical connection to each of the electrodes, the second electrode including a plurality of apertures to promote a more uniform current density distribution therein, whereby the first electrode and the first and second gel pads may function as a cardiac pacing electrode and the second electrode and the second gel pad may function as a cardiac defibrillation electrode.

16. A multi-function multi-electrode device which comprises first and second electrically conductive electrodes in substantially parallel spaced apart relationship, a first gel pad located between the first and second electrodes, a second gel pad located on or adjacent to the second electrode, the second gel pad being exposed or exposable for making contact with a patient, and means for making electrical connection to each of the electrodes, the first electrode including a plurality of apertures to promote a more uniform current density distribution therein, whereby the first electrode and the first and second gel pads may function as a cardiac pacing electrode and the second electrode and the second gel pad may function as a cardiac defibrillation electrode.

17. A multi-function multi-electrode device which comprises first and second electrically conductive electrodes in substantially parallel spaced apart relationship, a first gel pad located between the first and second electrodes, a second gel pad located on or adjacent to the second electrode, the second gel pad being exposed or exposable for making contact with a patient, an adhesive foam layer covering the first electrode and edges of the first and second gel pads, and means for making electrical connection to each of the electrodes, whereby the first electrode and the first and second gel pads may function as a cardiac pacing electrode and the second electrode and the second gel pad may function as a cardiac defibrillation electrode.

* * * * *